United States Patent
Kimmlingen

(10) Patent No.: US 11,181,593 B2
(45) Date of Patent: Nov. 23, 2021

(54) GRADIENT COIL ASSEMBLY FOR A MAGNETIC RESONANCE APPARATUS

(71) Applicant: Siemens Healthcare GmbH, Erlangen (DE)

(72) Inventor: Ralph Kimmlingen, Zirndorf (DE)

(73) Assignee: Siemens Healthcare GmbH, Erlangen (DE)

( * ) Notice: Subject to any disclaimer, the term of this patent is extended or adjusted under 35 U.S.C. 154(b) by 650 days.

(21) Appl. No.: 15/983,496

(22) Filed: May 18, 2018

(65) Prior Publication Data

US 2018/0335493 A1    Nov. 22, 2018

(30) Foreign Application Priority Data

May 18, 2017  (EP) ..................... 17171672

(51) Int. Cl.
| | |
|---|---|
| *G01R 33/385* | (2006.01) |
| *G01R 33/3875* | (2006.01) |
| *G01R 33/022* | (2006.01) |
| *A61B 5/055* | (2006.01) |
| *G01R 33/421* | (2006.01) |

(52) U.S. Cl.
CPC ......... *G01R 33/3856* (2013.01); *A61B 5/055* (2013.01); *G01R 33/022* (2013.01); *G01R 33/385* (2013.01); *G01R 33/3858* (2013.01); *G01R 33/3875* (2013.01); *G01R 33/4215* (2013.01)

(58) Field of Classification Search
CPC .......... G01R 33/3856; G01R 33/385; G01R 33/022; G01R 33/3858; G01R 33/3875; G01R 33/4215
See application file for complete search history.

(56) References Cited

U.S. PATENT DOCUMENTS

| | | | | |
|---|---|---|---|---|
| 5,334,937 A | * | 8/1994 | Peck ................... | G01R 33/385 324/318 |
| 2003/0197507 A1 | | 10/2003 | Liu | |
| 2005/0179434 A1 | | 8/2005 | Goldie et al. | |
| 2012/0119741 A1 | * | 5/2012 | Kimmlingen ...... | G01R 33/3856 324/318 |
| 2013/0075068 A1 | | 3/2013 | Huber et al. | |
| 2015/0346296 A1 | | 12/2015 | Biber et al. | |
| 2016/0091576 A1 | | 3/2016 | Tomiha et al. | |

FOREIGN PATENT DOCUMENTS

| | | |
|---|---|---|
| EP | 0587423 A1 | 3/1994 |
| JP | 2011010760 A | 1/2011 |

OTHER PUBLICATIONS

English translation of JP 2011/010760 provided by Espacenet. (Year: 2021).*

* cited by examiner

*Primary Examiner* — Rishi R Patel

(74) *Attorney, Agent, or Firm* — Schiff Hardin LLP

(57) ABSTRACT

A gradient coil assembly for a magnetic resonant apparatus has a primary coil and a secondary coil, wherein the primary coil has a first primary coil winding and a second primary coil winding, wherein the first primary coil winding and the second primary coil winding are electrically connected to a voltage source and are jointly designed to generate a magnetic field gradient in a direction when the voltage source induces a current in those windings.

14 Claims, 5 Drawing Sheets

(Prior Art)

GRADIENT COIL ASSEMBLY FOR A MAGNETIC RESONANCE APPARATUS

BACKGROUND OF THE INVENTION

Field of the Invention

The invention concerns a gradient coil assembly having a primary coil with a first primary coil winding and a second primary coil winding, which are jointly designed to generate a magnetic field gradient in a first direction.

Description of the Prior Art

In a magnetic resonance device, the body of an examination object, in particular a patient, is exposed to a strong basic magnetic field, for example 1.5 or 3 tesla, with the use of a basic field magnet. During acquisition of magnetic resonance raw data (MR imaging), gradient pulses are applied with the use of a gradient coil assembly. With suitable antenna devices, a radio-frequency (RF) antenna unit emits radio-frequency pulses (RF pulses), in particular excitation pulses, that cause nuclear spins of specific atoms to be excited into resonance by these RF pulses and thereby tilted through a defined flip angle relative to the magnetic field lines of the basic magnetic field. Upon relaxation of the nuclear spins, radio-frequency signals, called magnetic resonance signals, are emitted, and are received by suitable radio-frequency antennas, and then further processed. Finally, the desired image data can be reconstructed from the raw data acquired in this way.

A gradient coil assembly typically has three primary coils and three secondary coils respectively corresponding thereto. A primary coil is typically designed to generate a magnetic field gradient in one spatial direction. A secondary coil corresponding thereto screens the magnetic field gradient generated by the primary coil such that this is compensated outside the gradient coil assembly and/or no magnetic field gradient forms outside the gradient coil assembly. The primary coils and the secondary coils are activated with electric currents with amplitudes of up to 1 kA, which are subject to frequent and rapid changes in the direction of current with rising and falling rates of several 100 kA/s. The driving voltage for the coil current is up to several kV.

A gradient coil assembly is typically characterized by its maximum achievable gradient amplitude defined by the quotient of magnetic flux density and length. A further characteristic of its power is the slew rate. The slew rate is defined as the quotient of the maximum gradient amplitude and the time required to achieve the maximum gradient amplitude. Hence, the slew rate is a measure of the velocity of gradient coil assemblies. The maximum achievable gradient amplitude and the slew rate define the maximum gradient moment that can be generated by the gradient coil assembly within a time period. The gradient moment is proportional to the time integral of the time-dependent gradient amplitude. A gradient coil assembly is also characterized by its nominal gradient amplitude. The nominal gradient amplitude is the maximum gradient amplitude to be generated in thermal equilibrium of the gradient coil assembly, taking its cooling into account.

The slew rate of a gradient coil assembly for a whole-body system is typically limited by a requirement not to cause stimulation of the peripheral nerves of the patient, to about 150/m/s to 200 T/m/s. The nominal gradient amplitude is typically limited by the maximal available cooling capacity by which the heat generated during the operation of the gradient coil assembly is dissipated. The nominal gradient amplitude of a clinical whole-body system is typically limited to 20 mT/m to 40 mT/m. This also limits the gradient moment that can be generated per time unit. New developments in the field of gradient-echo-based neuro applications are typically limited by the gradient moments that can be generated per time unit. To date, further developments of gradient coil assemblies mainly relate to the cooling of the gradient coil assemblies, such as, for example, DE 10 2013 208 631 B3 and DE 10 2011 083 204 A1.

SUMMARY OF THE INVENTION

An object of the present invention is to provide a gradient coil assembly that generates a strong gradient moment per time unit in an efficient manner.

The gradient coil assembly according to the invention has a first primary coil and a first secondary coil, wherein the first primary coil has a first primary coil winding and a second primary coil winding. The first primary coil winding and the second primary coil winding are electrically connected to a first voltage source and jointly generate a magnetic field gradient in a first direction when the first voltage source induces a first current in those windings.

The first primary coil is accordingly designed to generate a magnetic field gradient in a first direction when a first current is conducted in the first primary coil winding and the second primary coil winding. A primary coil winding typically has one or more conductor windings arranged in a saddle shape. A primary coil winding can also have a spiral-shaped conductor arrangement. The first primary coil winding, the second primary coil winding (and a coil winding in general) are typically arranged on a jacket surface of a circular cylinder. Further geometries such as ellipses, flat surfaces or a cone are conceivable. The radial distance of the second primary coil winding from the center of gradient coil assembly is typically different from the radial distance of the first primary coil winding. The first primary coil winding, the second primary coil winding and/or a coil winding generally are typically designed as coils that are connected to a voltage source and/or have inductance. The first primary coil, the first secondary coil and the first voltage source are typically electrically connected to one another such that they jointly form a first circuit.

The first primary coil winding and the second primary coil winding have respective conductors that are similarly arranged and/or deformed. The first primary coil winding and the second primary coil winding preferably differ in the radial distance and/or in distances between different subregions of the conductor. The second primary coil winding can originate from the first primary coil winding, for example from a centric elongation. The first primary coil winding typically differs from the second primary coil winding.

An advantage of the gradient coil assembly according to the invention is that the division of the first primary coil into a first primary coil winding and a second primary coil winding, with an unchanged first voltage source, enables the generation of a higher gradient amplitude, in particular a higher nominal gradient amplitude. The gradient coil assembly according to the invention can be activated by a conventional gradient controller serving as the first voltage source. The gradient coil assembly according to the invention can be activated by conventional software. Moreover, activation of the gradient coil assembly according to the invention with two primary coil windings requires only one voltage source and one amplifier. Consequently, the technical outlay is low compared to a gradient coil having a number of multi-layer primary coils and/or secondary coils.

The use of the first primary coil winding and the second primary coil winding enables the ohmic resistance of the first primary coil to be reduced compared to a conventional primary coil with only one primary coil winding, thus enabling the gradient coil assembly according to the invention to be activated in a particularly efficient manner. Similarly, the magnetic field gradient can be generated particularly efficiently in the first direction.

Increasing the gradient amplitude, in particular the nominal gradient amplitude, enables the gradient coil assembly according to the invention to generate a particularly high gradient moment per time unit with an unchanged slew rate. This improves the power of the gradient coil assembly according to the invention without increasing the risk of stimulation of the patient's peripheral nerves. Compared to a primary coil with only one primary coil winding, the first primary coil with the first primary coil winding and the second primary coil winding in particular only has a low additional space requirement of about 5 mm to 10 mm so that the gradient coil assembly according to the invention can be easily integrated in existing magnetic resonance devices. Generally, the efficiency of a primary coil and hence the efficiency of the gradient coil assembly increases as the radial distance between the primary coil and a corresponding secondary coil increases. Consequently, the greater the radial distance between the primary coil and the corresponding secondary coil, the more efficiently a gradient coil assembly can be activated.

Even when it has a number of primary coils and secondary coils, a gradient coil assembly typically has a coil distance range between the set of primary coils and the set of secondary coils. The coil distance range is typically free of coil windings. Consequently, the gradient coil assembly according to the invention can be constructed such that the first and/or the second primary coil winding lie within the region provided as a coil distance range with a conventional gradient coil assembly. Nevertheless, the efficiency of the gradient coil assembly can be retained due to the division of the first primary coil. Consequently, the spatial dimensions of the gradient coil assembly according to the invention can be selected such that they correspond to the spatial dimensions of a conventional gradient coil assembly with a primary coil with only one primary coil winding. The gradient coil assembly according to the invention utilizes the spatial dimensions particularly efficiently. Consequently, there is no need to adapt the gradient control unit and/or the magnetic resonance device to the gradient coil assembly according to the invention. Consequently, the gradient coil assembly according to the invention can be particularly cost-effective to use.

Depending upon the requirement for a required maximum and/or nominal gradient amplitude, the arrangement of the first primary coil winding and the second primary coil winding can be connected in parallel or in series to the first voltage source. For the first secondary coil, it is possible to select series connection to the first primary coil thus enabling the first voltage source to be retained. Alternatively, the first primary coil and/or the first secondary coil can be connected to a further voltage source, which is different from the first voltage source. For reasons that are explained below, this further voltage source will be referred to as a third voltage source. Consequently, the first circuit can have the first voltage source and the third voltage source. The first voltage source and the third voltage source can be connected in series or in parallel. Alternatively, the first voltage source can form a first circuit with the first primary coil and the third voltage source can form a third circuit with the first secondary coil. The use of the first voltage source and the third voltage source particularly efficiently enables the slew rate to be increased to, for example, more than 200 T/m/s. This is particularly advantageous for methods for MR imaging, which require a low maximum gradient amplitude of, for example, less than 15 mT/m with a minimum rise time, such as, for example, spiral sequences or blipped EPI. The higher power loss due to the higher frequencies of the gradient pulses can be compensated by doubling the cooling capacity.

In an embodiment of the gradient coil assembly, the first cooling layer is assigned to the first primary coil winding and a second cooling layer is assigned to the second primary coil winding.

A cooling layer is typically an arrangement containing a cooling medium. The cooling medium can preferably circulates within the cooling layer. The circulation of the cooling medium can take place actively and/or passively. For this purpose, the cooling layer can have cooling hoses and/or further hollow shapes, wherein the cooling medium can circulate within these cooling hoses and/or further hollow shapes. The cooling medium is preferably a liquid or a gas. The cooling medium preferably has a particularly high thermal capacity. If a cooling layer, for example the first cooling layer, of a coil winding, is assigned, for example, to the first primary coil winding, the cooling layer dissipates the heat that forms during the operation of the gradient coil assembly, in particular when the coil winding is activated by a current, for example on induction of the first current. The cooling layer assigned to a coil winding preferably lies on a wide area of the coil winding and/or abuts this and/or is interleaved therewith over a wide area. The cooling capacity of a cooling layer is primarily used to cool the coil winding assigned thereto, in particular during the operation thereof. Preferably 70%, and more preferably 80%, of the cooling capacity of a cooling layer is used to cool the coil winding assigned thereto.

The first cooling layer is typically different from the second cooling layer. The cooling capacity of the first cooling layer typically approximately corresponds to the cooling capacity of the second cooling layer. The first cooling layer is preferably embodied similarly to the second cooling layer. In particular, the first cooling layer and the second cooling layer can have the same functions and/or geometry. The assignment and/or connection and/or interleaving of the second cooling layer with the second primary coil winding is preferably similar to the assignment and/or connection and/or interleaving of first cooling layer to/with the first primary coil winding.

Consequently, according to this embodiment, two cooling layers are assigned to the first primary coil so that the first primary coil can be cooled particularly efficiently. This enables the cooling capacity to be doubled compared to a conventional gradient coil assembly with a conventional primary coil that is not divided into a first primary coil winding and a second primary coil winding. This enables the nominal gradient amplitude to be increased by about 40%. As a result, the gradient coil assembly can be activated particularly efficiently and the magnetic field gradient can be generated particularly efficiently in the first direction.

In an embodiment of the gradient coil assembly, the gradient coil assembly has a second primary coil with a third primary coil winding, wherein the third primary coil winding is connected in series to a second voltage source and generates a magnetic field gradient in a second direction when the second voltage source induces a second current in those windings.

The second direction is preferably orthogonal to the first direction. According to this embodiment, the second primary coil corresponds to a typical conventional gradient coil assembly. According to this embodiment, the gradient coil assembly combines a conventional primary coil with the first primary coil comprising the first primary coil winding and the second primary coil winding. The first primary coil differs from the second primary coil. The second primary coil preferably does not include any further primary coil winding in addition to the third primary coil winding. The third primary coil winding is preferably the sole primary coil winding formed by the second primary coil.

Consequently, it is possible for a magnetic field gradient with a particularly high amplitude to be generated in the first direction. This is particularly advantageous for functional MR imaging, for example by use of the BOLD method, since the head of each patient is typically oriented and/or positioned in the same way within the gradient coil assembly. Consequently, an MR control sequence to be executed can be selected such that the direction with the greatest demand on the gradient coil assembly corresponds to the first direction. In echoplanar MR imaging, this is, for example, the x-direction, i.e. typically the horizontal direction perpendicular to the cylinder axis of the gradient coil assembly. For physiological reasons, constant orientation of the read-out gradients in the x-direction has become established. Optimum results are achieved when the amplitude and/or the slew rate of the magnetic field gradient are particularly high in the x-direction. The first direction preferably corresponds to the x-direction. The first direction can alternatively correspond to another direction in which an MR control sequence places particularly high demands on the gradient coil assembly.

The simplified structure of the second primary coil enables a selective improvement to the first primary coil. The second primary coil can be produced in a space-saving and/or cost-effective way. The efficiency of the second primary coil preferably corresponds to the efficiency of a conventional primary coil. The gradient coil assembly can have at least one further primary coil with a further secondary coil assigned thereto, wherein the further primary coil has a similar design to the second primary coil. A gradient coil assembly according to this embodiment is focused on improving and/or increasing the efficiency of the first primary coil, which generates a magnetic field gradient in the first direction. Preferably, a number of MR control sequences requires a particularly high gradient amplitude in the first direction. The coil distance range is not reduced by an additional primary coil winding of the second primary coil. As a result, the efficiency of the gradient coil is unit at least retained, or increased.

In another embodiment of the gradient coil assembly, in the presence of the first current, a current density in the first primary coil winding and/or the second primary coil winding is maximum 70% of the current density in the third primary coil winding in the presence of the second current.

In this embodiment, the first primary coil winding and the second primary coil winding are preferably connected in parallel to the first voltage source. The first current emanates from the first voltage source and is typically split between the first primary coil winding and the second primary coil winding. The first magnetic field gradient is generated by the first primary coil winding and the second primary coil winding based on the first current. If the third primary coil winding generates the second magnetic field gradient based on the second current and if the amplitude of the second magnetic field gradient corresponds to the amplitude of the first magnetic field gradient, the current density in the first primary coil winding and/or the second primary coil winding is preferably maximum 70%, preferably maximum 60%, particularly preferably maximum 55% of the current density in the third primary coil winding. If the first current corresponds to the second current, the current density in the first primary coil winding and/or the second primary coil winding is preferably maximum 70%, preferably maximum 60%, particularly preferably maximum 55% of the current density in the third primary coil winding.

According to this embodiment, the ohmic resistance of the first primary coil is maximum 70%, preferably maximum 60%, particularly preferably maximum 55% as high as the ohmic resistance of the second primary coil. As a result, with the same power input, the first primary coil can generate a magnetic field gradient with a higher amplitude than the second primary coil.

One embodiment of the gradient coil assembly provides that the gradient coil assembly comprises a third cooling layer assigned to the third primary coil winding. Consequently, the second primary coil is preferably assigned to precisely one cooling layer. The cooling capacity of the third cooling layer typically approximately corresponds to the cooling capacity of the second and/or first cooling layer. The third cooling layer is preferably designed similarly to the first cooling layer. The assignment and/or connection and/or interleaving of the third cooling layer to/with the third primary coil winding is preferably similar to the assignment and/or connection and/or interleaving of first cooling layer to/with the first primary coil winding.

The simplified structure of the second primary coil and the assignment of a third cooling layer enables a selective improvement to the first primary coil. The second primary coil with the third cooling layer can be produced in a space-saving and/or cost-effective way. The efficiency of the second primary coil preferably corresponds to the efficiency of a conventional primary coil.

In another embodiment of the gradient coil assembly, the first secondary coil has a first secondary coil winding, wherein the first secondary coil winding is connected in series to the first voltage source and effects a screening of the magnetic field gradient in the first direction when the first voltage source induces the first current.

The first secondary coil typically forms, together with the first primary coil and the first voltage source, a first circuit, wherein this circuit preferably is a series circuit. The first secondary coil preferably corresponds to a conventional secondary coil, which only has a secondary coil winding. Preferably, a fifth cooling layer is assigned to the first secondary coil. Generally, a secondary coil typically has half the number of windings of the primary coil assigned thereto. Consequently, the number of windings in the first secondary coil, in particular the first secondary coil winding, is preferably half the number of windings in the first primary coil. The amplitude of the magnetic field to be generated by the first secondary coil to be generated is typically lower than the amplitude of the magnetic field gradient to be generated by means of the first primary coil. Consequently, the power input and/or power output to the first secondary coil is typically lower than to the first primary coil. Consequently, with the first secondary coil, it is possible to dispense with a design similar to the first primary coil having two coil windings and two cooling layers without this limiting the efficiency of the gradient coil assembly. According to this embodiment, the gradient coil assembly has a particularly space-saving design and be produced cost-effectively.

In another embodiment of the gradient coil assembly, the first primary coil winding and the second primary coil winding are connected in parallel to the first voltage source. The parallel circuit according to this embodiment effects a reduction of the current density in the first primary coil winding and/or the second primary coil winding. The first current, which is required to generate the magnetic field gradient in the first direction, preferably corresponds to the current from a conventional first primary coil required to generate the magnetic field gradient in the first direction. According to this embodiment, the ohmic resistance of the first primary coil is reduced with simultaneously improved cooling capacity. Consequently, this embodiment of the gradient coil assembly is particularly efficient.

In another embodiment of the gradient coil assembly, the first primary coil winding and the second primary coil winding are connected in series to the first voltage source. Herein, the first primary coil winding and the second primary coil winding preferably jointly have a number of windings approximately corresponding to the number of windings in a primary coil comprised by a conventional gradient coil assembly. Herein, the first primary coil winding and the second primary coil winding preferably each have a number of windings corresponding to approximately half the number of windings in a primary coil formed by a conventional gradient coil assembly. The division of the first primary coil into the first primary coil winding and the second primary coil winding according to this embodiment enables increased cooling capacity for conductors comprised by the primary coil thus improving the efficiency of the gradient coil assembly.

The invention furthermore encompasses a gradient system having a gradient coil assembly according to the invention as described above, and a first voltage source. The first voltage source is electrically connected to the first primary coil winding and second primary coil winding comprised by the gradient coil assembly. The first primary coil winding and the second primary coil winding are jointly designed to generate a magnetic field gradient in a first direction when the first voltage source induces a first current in those windings. Embodiments of the gradient system according to the invention are similar to the embodiments of the gradient coil assembly according to the invention. The gradient system can also have a second voltage source, which is switched in series with the third primary coil winding of the gradient coil assembly, wherein the third primary coil winding is designed to generate a magnetic field gradient in a second direction when the second voltage source induces a second current therein. The first voltage source is designed specifically for the requirements of the first primary coil according to the invention. The second voltage source is a voltage source of the type suitable for operating a conventional gradient coil assembly.

The invention furthermore encompasses a magnetic resonance apparatus having a scanner with a gradient system according to the invention as described above. The scanner has a basic field magnet, a radio-frequency antenna, a first primary coil of the gradient coil system with a first primary coil winding and a second primary coil winding, a first secondary coil of the gradient coil system, and a first voltage source of the gradient coil system, electrically connected to the first primary coil winding and the second primary coil winding.

The first primary coil winding and the second primary coil winding are jointly designed to generate a magnetic field gradient in a first direction when the first voltage source induces a first current in those windings.

The gradient system according to the invention and/or the gradient coil assembly according to the invention can be integrated in the magnetic resonance scanner. The gradient system according to the invention and/or the gradient coil assembly according to the invention can also be independently manufactured components that are installed in the magnetic resonance scanner. Embodiments of the magnetic resonance apparatus according to the invention are similar to the embodiments of the gradient system according to the invention and/or the gradient coil assembly according to the invention. The magnetic resonance apparatus can have further control components that are necessary and/or advantageous.

In an embodiment of the magnetic resonance apparatus, a defined hollow cylindrical distance range in the scanner between the basic field magnet and the RF antenna contains the gradient coil assembly with the first primary coil having the first primary coil winding and the second primary coil winding. Consequently, to integrate the gradient coil assembly according to the invention in the scanner, it is necessary for the maximum external dimensions of the gradient coil assembly according to the invention to correspond to the hollow-cylindrical distance range. In this case, the gradient coil assembly according to the invention can replace a conventional gradient coil assembly provided for the magnetic resonance scanner and/or be exchanged therewith. Consequently, it is then also possible for an existing magnetic resonance scanner (apparatus) to be retrofitted with the gradient coil assembly according to the invention. In addition, it is not necessary to adapt an additional component of the magnetic resonance scanner to the gradient coil assembly according to the invention.

The invention furthermore encompasses a method for designing a first primary coil winding and a second primary coil winding of a first primary coil of a gradient coil assembly that includes the first primary coil and a first secondary coil, wherein the first primary coil winding and the second primary coil winding are electrically connected to a first voltage source. The method has the steps of specifying, for a computer, a magnetic field gradient in a first direction, determining a geometry and/or an electrical property of the first primary coil winding and the second primary coil in the computer winding such that, when a first current is induced in the first and secondary coil windings by the first voltage source, the magnetic field gradient is generated in the first direction jointly by the first primary coil winding and the second primary coil winding.

Consequently, the method according to the invention describes a method for designing a gradient coil assembly according to the invention. The geometry and/or electric properties of the first primary coil are determined on the basis of the specified magnetic field gradient in a first direction, typically by execution of an optimization method. Typically at least one boundary condition is taken into account in this method. A boundary condition can include, for example, a linearity and/or sensitivity of the magnetic field gradient in the first direction and/or a maximum current density. The magnetic field gradient in the first direction typically corresponds to a magnetic field gradient generated by a conventional gradient coil in a direction corresponding to the specified first direction.

Advantages of the magnetic resonance apparatus according to the invention, the gradient system according to the invention and the method according to the invention substantially correspond to the advantages of the gradient coil assembly according to the invention, as explained in detail above. Features, advantages and alternative embodiments noted for the gradient coil assembly are applicable to the other aspects of the invention as well.

DESCRIPTION OF THE PREFERRED EMBODIMENTS

Figure 1:
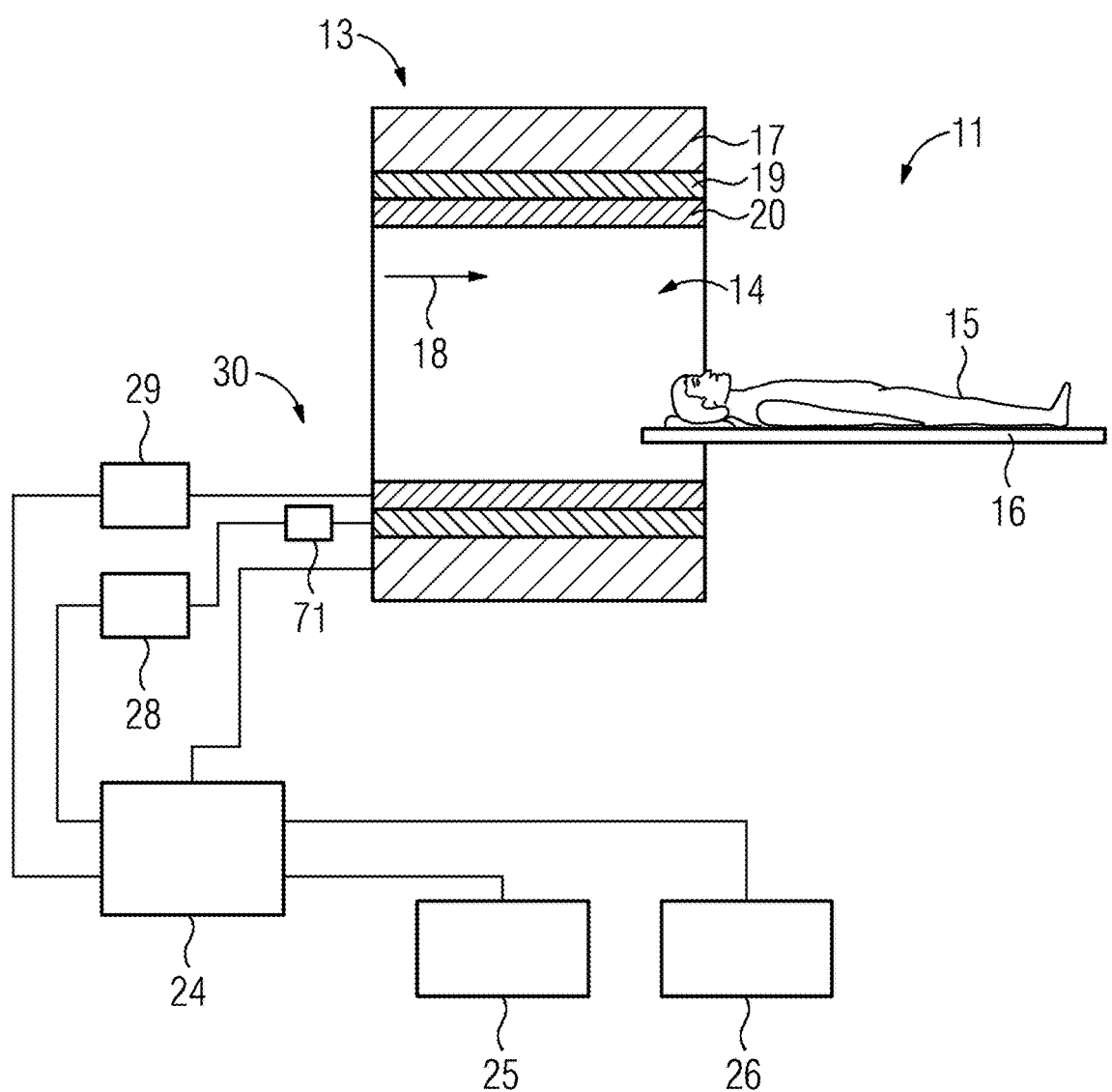
FIG. 1 schematically illustrates a magnetic resonance apparatus according to the invention.

FIG. 1 shows a magnetic resonance apparatus 11 according to the invention. The magnetic resonance apparatus 11 has an MR data acquisition scanner 13 with a basic field magnet 17 that generates a strong and constant basic magnetic field 18. The scanner 13 has a cylindrical patient-receiving region 14 for receiving a patient 15. The patient-receiving region 14 is enclosed in a circumferentially by the scanner 13 so as to have a cylindrical shape. The patient 15 can be moved into the patient-receiving region 14 by a patient support 16. The patient support 16 has a patient table that is movable within the scanner 13.

The scanner 13 also has an RF antenna 20, which, in the shown embodiment, is a fixed integrated body coil in the scanner 13, and an RF antenna controller 29 that activates the RF antenna 20 so as to radiate radio-frequency pulses into an examination volume substantially formed by the patient-receiving region 14. The emitting radio-frequency pulses cause certain nuclear spins in the patient 15 to be deflected by a defined amount, known as a flip angle, from the field lines of the basic magnetic field 18. As those excited nuclear spins relax and return to the steady state, they emit radio-frequency signals called MR signals, which are detected by the same antenna from which the excitation pulses were radiated, or by a different antenna.

Between the basic field magnet 17 and the radio-frequency antenna 20, the scanner 13 a hollow-cylindrical distance range. The hollow-cylindrical distance range is typically designed such that a conventional, i.e. non-inventive, gradient coil assembly can be positioned therein for spatially encoding the MR signals. The external geometry and/or external dimensions of the gradient coil assembly 19 according to the invention 19 are such that it can be arranged in the hollow-cylindrical distance range between the basic field magnet 17 and the radio-frequency antenna 20. The scanner 13 has a gradient coil assembly 19 according to the invention. The gradient coil assembly 19 is connected to the first voltage source 71 and is activated by a gradient controller 28. The gradient coil assembly 19 and the first voltage source 71 together form the gradient system 30 according to the invention. The gradient system 30 can also include the gradient controller 28.

To control the basic field magnet 17, the gradient controller 28 and the radio-frequency antenna controller 29, the magnetic resonance apparatus 11 has a control computer 24.

The control computer 24 centrally controls the magnetic resonance apparatus 11, such as in the performance of MR control sequences. The magnetic resonance apparatus 11 has a display unit 25. The magnetic resonance apparatus 11 also has an input unit 26 via which information and/or control parameters can be entered by a user during a scanning procedure. The control computer 24 can include the gradient controller 28 and/or radio-frequency antenna controller 29 and/or the display unit 25 and/or the input unit 26.

The magnetic resonance apparatus 11 depicted can obviously have further components that are usually present in magnetic resonance apparatuses. The general mode of operation of a magnetic resonance apparatus is known to those skilled in the art so that a more detailed description is not necessary herein.

Figure 2:
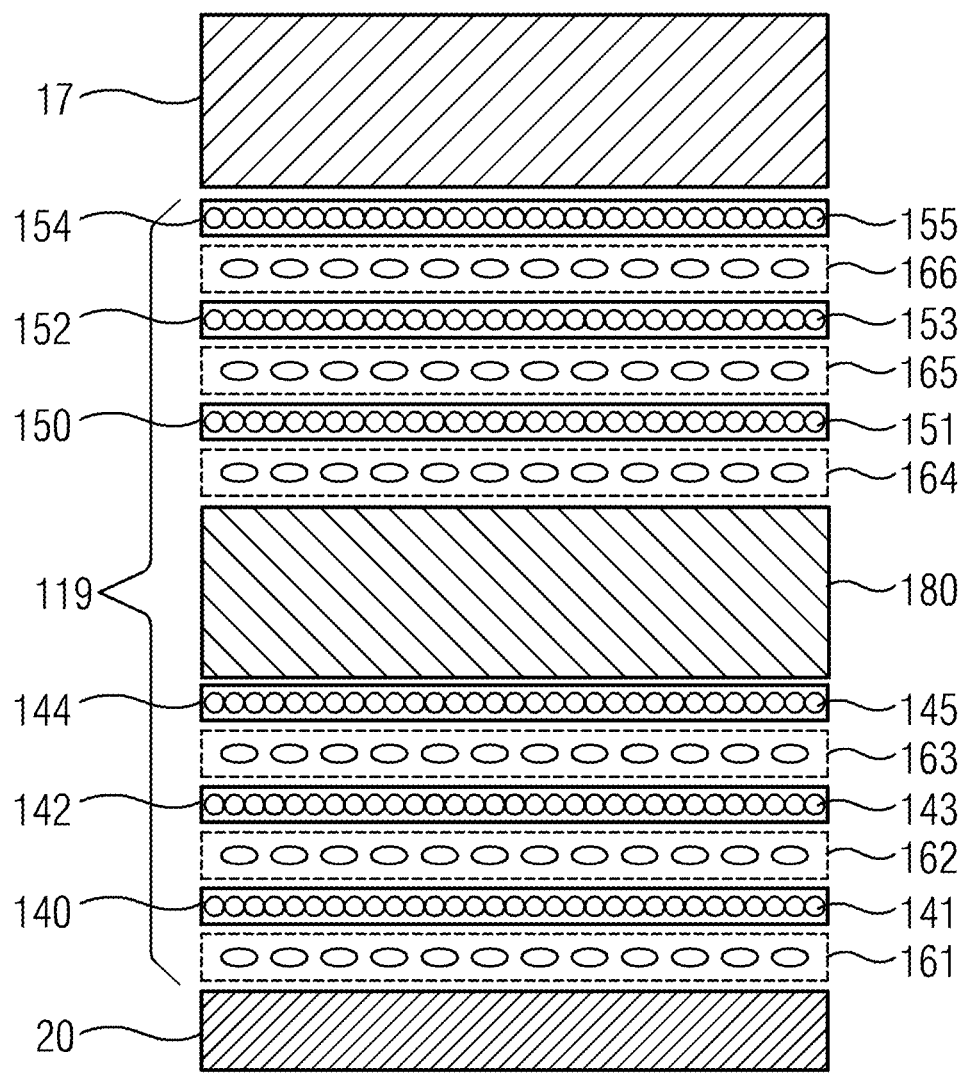
FIG. 2 schematically illustrates a gradient coil assembly known from the prior art.

FIG. 2 shows a radial structure of a gradient coil assembly 119 known from the prior art, i.e. a conventional gradient coil assembly, surrounded by the basic field magnet 17 and the radio-frequency antenna 20 of a conventional scanner. Compared to the view in FIG. 1, the view of the conventional gradient coil assembly 119 is reduced to a half plane bounded by the cylinder axis of the conventional gradient coil assembly 119. Between the basic field magnet 17 and the radio-frequency antenna unit 11, there is a defined hollow cylindrical distance range, which is filled by the conventional gradient coil assembly 119.

The components of the conventional gradient coil assembly 119 are arranged radially outwardly with the following sequence:

a first cooling layer 161 for a first primary coil 140,
the first primary coil 140 with a first primary coil winding 141,
a second cooling layer 162 for a second primary coil 142,
the second primary coil 142 with a second primary coil winding 143,
a third cooling layer 163 for a third primary coil 144,
the third primary coil 144 with a third primary coil winding 145,
a coil distance range 180, which separates the primary coils 140, 142, 144 from the secondary coils 150, 152, 154,
a fourth cooling layer 164 for a first secondary coil 150,
the first secondary coil 150 with a first secondary coil winding 151,
a second cooling layer 165 for a second secondary coil 152,
the second secondary coil 152 with a second secondary coil winding 153,
a third cooling layer 166 for a third secondary coil 154,
the third secondary coil 154 with a third secondary coil winding 155.

The first primary coil 140 is designed to generate a magnetic field gradient in a first spatial direction and the first secondary coil 150 is designed to screen the magnetic field gradient in the first spatial direction. The second primary coil 142 is embodied to generate a magnetic field gradient in a second spatial direction and the second secondary coil 152 is designed to screen the magnetic field gradient in the second spatial direction. The third primary coil 144 is designed to generate a magnetic field gradient in a third spatial direction and the third secondary coil 154 is designed to screen the magnetic field gradient in the third spatial direction.

Figure 3:
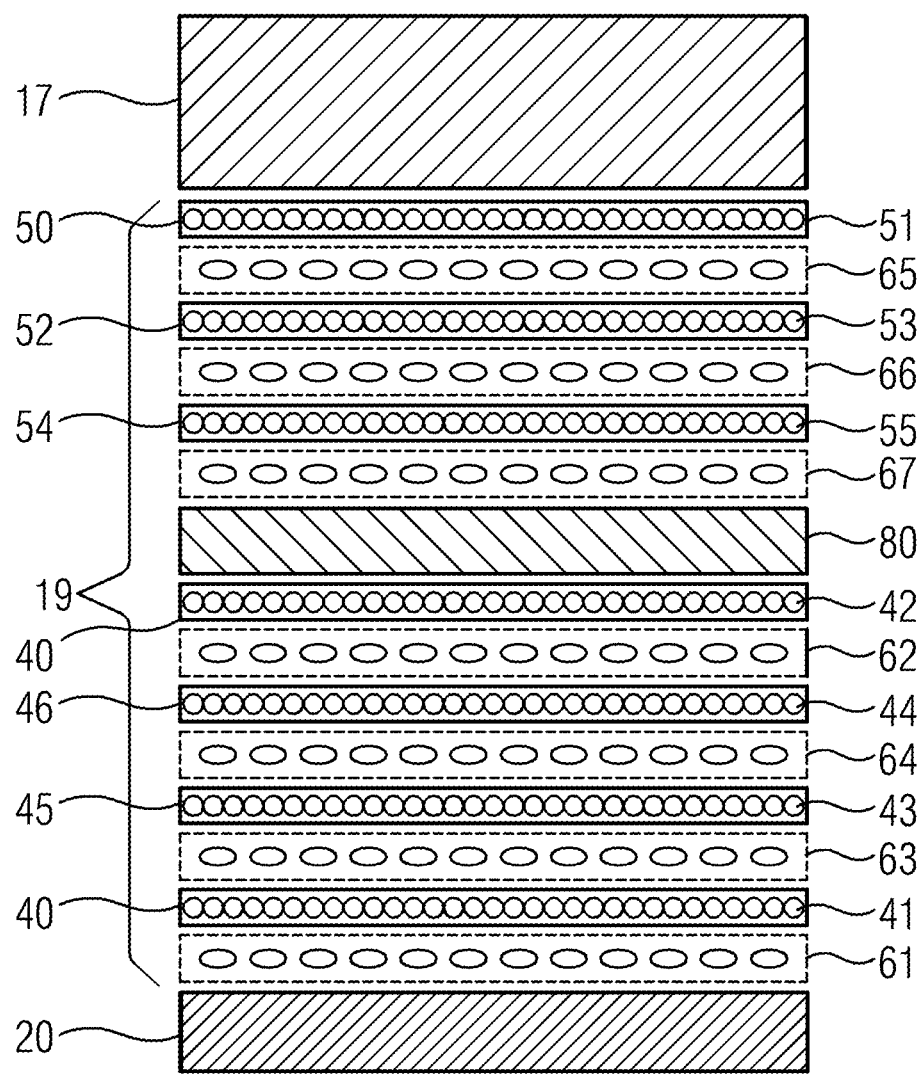
FIG. 3 schematically illustrates a first embodiment of a gradient coil assembly according to the invention.

FIG. 3 shows a radial structure of a gradient coil assembly 19 according to the invention surrounded by the basic field magnet 17 and the radio-frequency antenna 20 of the scanner 13. Compared to the view in FIG. 1, the view of the gradient coil assembly 19 is reduced to a half plane bounded by the cylinder axis of the gradient coil assembly 19. Between the basic field magnet 17 and the radio-frequency antenna unit 11, there is a defined hollow cylindrical distance range, which preferably corresponds to the defined hollow-cylindrical distance range in the conventional embodiment in FIG. 2. This defined hollow-cylindrical distance range is preferably filled by the gradient coil assembly 19 according to the invention. The external geometric dimensions of the gradient coil assembly 19 according to the invention preferably correspond to the external geometric dimensions of the conventional gradient coil assembly 119.

The gradient coil assembly 19 has the following components arranged radially outwardly in the following sequence:
- a first cooling layer 61 for a first primary coil winding 41 comprised by the first primary coil 40,
- the first primary coil winding 41,
- a third cooling layer 63 for a second primary coil 45,
- the second primary coil 45 with a third primary coil winding 43,
- a fourth cooling layer 64 for a third primary coil 46,
- the third primary coil 46 with a fourth primary coil winding 44,
- a second cooling layer 62 for a second primary coil winding 42 comprised by the first primary coil 40,
- the second primary coil winding 42,
- a coil distance range 80, which separates the primary coils 40, 45, 46 from the secondary coils 50, 52, 54,
- a seventh cooling layer 67 for a second secondary coil 54,
- the second secondary coil 54 with a second secondary coil winding 55,
- a sixth cooling layer 66 for a third secondary coil 52,
- the third secondary coil 52 with a third secondary coil winding 53,
- a fifth cooling layer 65 for a first secondary coil 50,
- the first secondary coil 50 with a first secondary coil winding 51.

Each of the windings of the gradient coil assembly 19 has electrical connectors for connecting that winding to a designated voltage source, as described below.

A cooling layer for a coil and/or for a coil winding is assigned to this coil and/or coil winding. Consequently, the first cooling layer 61 is, for example, assigned to the first primary coil winding 41. Consequently, the cooling layers 61, 62, 63, 64, 65, 66, 67 of the gradient coil assembly 19 are each assigned to a coil or coil winding and are consequently primarily embodied to cool the coil or coil winding assigned thereto. To this end, the coil or coil winding can be arranged interleaved with the cooling layer assigned thereto and/or transposed in the sequence described above.

The first primary coil 40 is designed to generate a magnetic field gradient in a first spatial direction and the first secondary coil 50 is designed to screen the magnetic field gradient in the first spatial direction. The second primary coil 45 is designed to generate a magnetic field gradient in a second spatial direction and the second secondary coil 54 is designed to screen the magnetic field gradient in the second spatial direction. The third primary coil 46 is designed to generate a magnetic field gradient in a third spatial direction and the third secondary coil 52 is designed to screen the magnetic field gradient in the third spatial direction.

The magnetic field gradient generated by the first secondary coil 50 typically has the same amplitude with different polarity as the magnetic field gradient generated by the first primary coil 40 so that the two magnetic field gradients would cancel each other out if the first primary coil 40 and the first secondary coil 50 were arranged at the same position. Due to a radial distance between the first primary coil 40 and the first secondary coil 50, when the first primary coil 40 and the first secondary coil 50 are activated, induction of the first current causes a magnetic field gradient unequal to zero to be generated in the patient-receiving region 14. The greater the radial distance between the first primary coil 40 and the first secondary coil 50, the greater the efficiency of the gradient coil assembly 19. The efficiency of a gradient coil assembly 19 can be defined by the quotient of the strength of the magnetic field gradient in the patient-receiving region 14 and the strength of the first current. The relationship given in this paragraph applies generally to a primary coil and a secondary coil assigned to the primary coil.

Compared to the conventional gradient coil 119, according to the structure depicted in FIG. 3, the radial distance between the second primary coil 45 and the second secondary coil 54 and the radial distance between the third primary coil 46 and the third secondary coil 52 are retained and are consequently preferably the same size. The radial distance between the middle radial position of the first primary coil 40 and the first secondary coil 50 increases. The coil distance range 80 has a smaller radial extension than the coil distance range 180 of the conventional gradient coil assembly 119. The external dimensions of the coil distance range 80, the second cooling layer 62 and the second primary coil winding 42 together preferably correspond to the external dimensions of the coil distance range 180 of the conventional gradient coil assembly 119.

Figure 4:
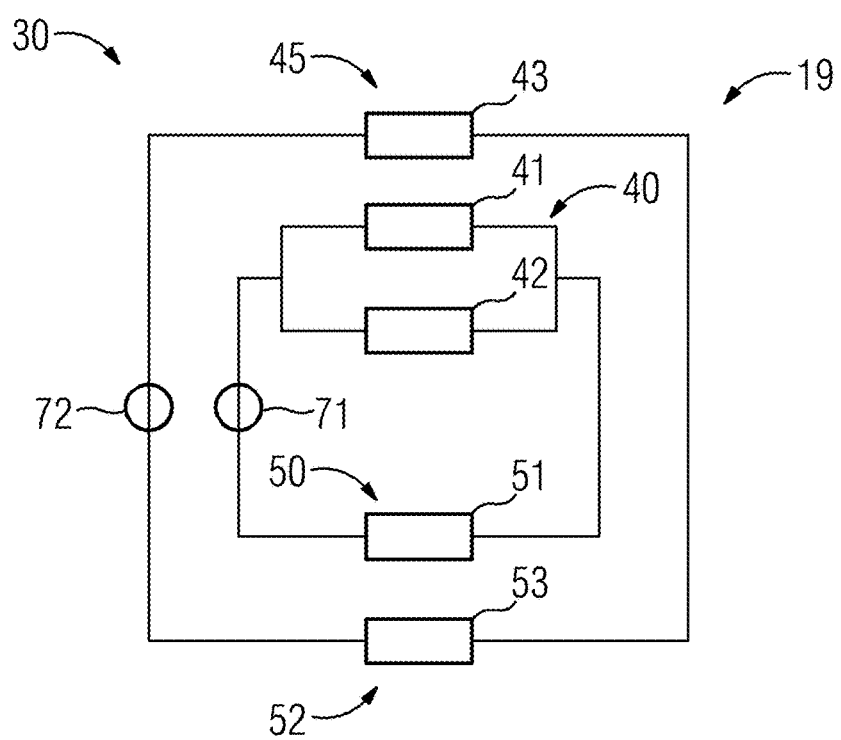
FIG. 4 is a circuit diagram of a first embodiment of a gradient system according to the invention.

FIG. 4 shows a circuit diagram of a first embodiment of a gradient system according to the invention 30. The gradient system has a first voltage source 71, a second voltage source 72 and a gradient coil assembly 19. The circuit diagram includes two circuits, wherein the first voltage source 71 and the second voltage source 72 are assigned to circuits that are different from each other.

The first circuit has the first voltage source 71, a first primary coil 40 with a first primary coil winding 41 and a second primary coil winding 42, and a first secondary coil 50 with a first secondary coil winding 51. The first secondary coil winding 51 is connected in series to the first voltage source 71 and the first primary coil 40. The first primary coil winding 41 and the second primary coil winding 42 are connected in parallel to the first voltage source 71. When the first voltage source 71 induces a first current, the first primary coil winding 41 and the second primary coil winding 42 are jointly embodied to generate a magnetic field gradient in a first direction. In this case, due to the first current, the first secondary coil winding 51 generates an opposing magnetic field, which effects screening of the magnetic field gradient in the first direction in particular outside the gradient coil assembly 19.

The second circuit has the second voltage source 72, a second primary coil 45 with a third primary coil winding 43 and a second secondary coil 52 with a second secondary coil winding 53. Herein, the second secondary coil winding 53 is connected in series to the second voltage source 72 and the second primary coil 45, i.e. also to the third primary coil winding 43. When the second voltage source 71 induces a second current, the third primary coil winding 43 is embodied to generate a magnetic field gradient in a second direction. In this case, due to the second current, the second secondary coil winding 53 generates an opposing magnetic field, which effects screening of the magnetic field gradient in the second direction in particular outside the gradient coil assembly 19.

In the presence of the first current, a current density in the first primary coil winding and/or the second primary coil winding is maximum 70%, preferably maximum 60%, particularly preferably maximum 55% of a current density in the third primary coil winding 43 in the presence of the second current. For this relationship, the first current at the output from the first voltage source 71 preferably corresponds to the second current at the output from the second voltage source 72. Generally, a temporal correlation of an output of the first current through the first voltage source 71 with an output of the second current through the second voltage source 72 is determined by the MR control sequence to be executed. The MR control sequence to be executed typically also determines the strength of the first current and the second current, wherein the strength generally varies over time.

The gradient system can be designed, for example, for the following values: the first current at the output from the first voltage source 71 is 500 A. The first primary coil is designed to generate a magnetic field gradient in the first direction with a sensitivity of 100 $\Omega$T/A/m. The ohmic resistance of the first primary coil 40 is 50 m$\Omega$ since the first current is divided between the first primary coil winding 41 and the second primary coil winding 42. The ohmic resistance of the first secondary coil 50 is 50 m$\Omega$ since the first secondary coil 50 has half the number of windings in the corresponding first primary coil 40. Two cooling layers 61, 62 are assigned to the first primary coil 40.

In contrast thereto, a conventional gradient system, or, for example, also the second circuit having the second voltage source 72, the second primary coil 45 and the second secondary coil 52 can be designed as follows:

The second current at the output from the second voltage source 72 is 500 A. The first primary coil is designed to generate a magnetic field gradient in the first direction with a sensitivity of 100 $\mu$T/A/m. The ohmic resistance of the second primary coil 45 is 100 m$\Omega$ since the second current can only be delivered to the third primary coil winding 43 and hence the current density is twice as high as in the first primary coil winding 41 or second primary coil winding 42. The ohmic resistance of the second secondary coil 52 is 50 m$\Omega$ since the second secondary coil 52 has half the number of windings in the corresponding second primary coil 45. Only one cooling layer, the third cooling layer 63, is assigned to the second primary coil 45.

Consequently, compared to the first circuit having the first voltage source 71, the first primary coil 40 and the first secondary coil 50, the second circuit has an overall ohmic resistance that is 50% higher and a cooling capacity for the primary coil that is reduced by 50%. As a result, in the first circuit, the nominal amplitude of the magnetic field gradient in the first direction can be increased by 25% compared to the nominal amplitude of the magnetic field gradient in the second direction, wherein the first voltage source 71 can be retained. The capacity limit of the first circuit is typically determined by the first voltage source 71 and/or an amplifier comprised by the first voltage source 71. Herein, a maximum current of a transistor bank, for example 25 kW, or a maximum power of a transformer, for example 38 kW, can have a limiting action.

If the first voltage source 71 is adapted to the improved cooling capacity, due to the ohmic resistance of the first circuit that is reduced by 33%, a current that is higher by a factor of $\sqrt{1.5}$ is possible. Doubling the cooling capacity enables a current that is $\sqrt{2}$ times as high. Overall, this enables the amplitude of the magnetic field gradient to be 1.7 times as high in the first direction as the amplitude of the magnetic field gradient in the second direction.

Figure 5:
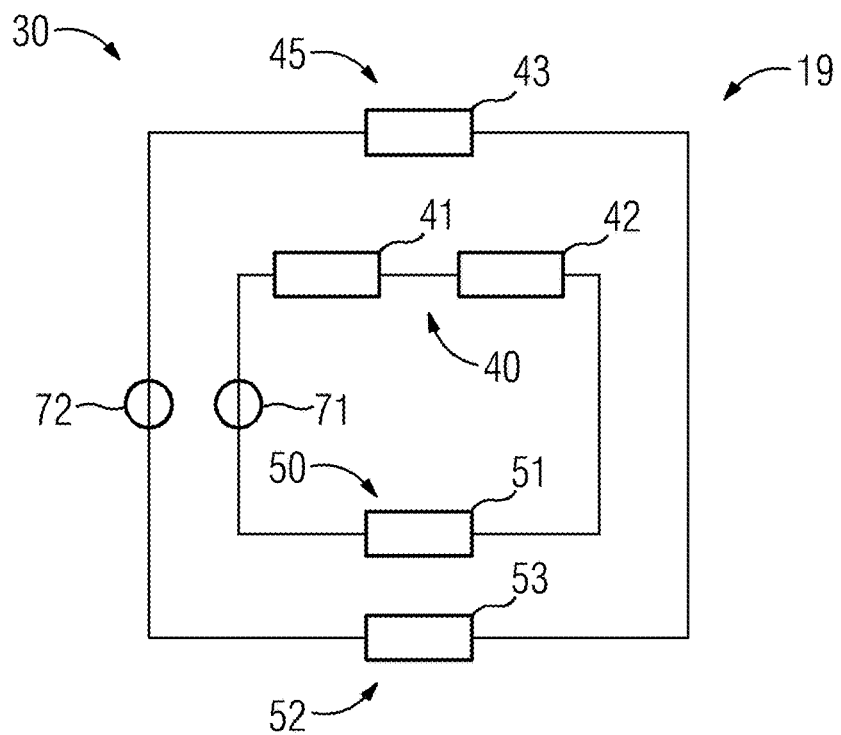
FIG. 5 is a circuit diagram of a second embodiment of a gradient system according to the invention.

FIG. 5 shows a circuit diagram of a second embodiment of a gradient system according to the invention 30. This differs from the circuit diagram depicted in FIG. 4 in the embodiment of the first primary coil 40. The first primary coil 40 includes the first primary coil winding 41 and the second primary coil winding 42, which are connected in series to the first voltage source 71. According to this embodiment, the first secondary coil 50 is also connected in series to the first voltage source 71.

Figure 6:
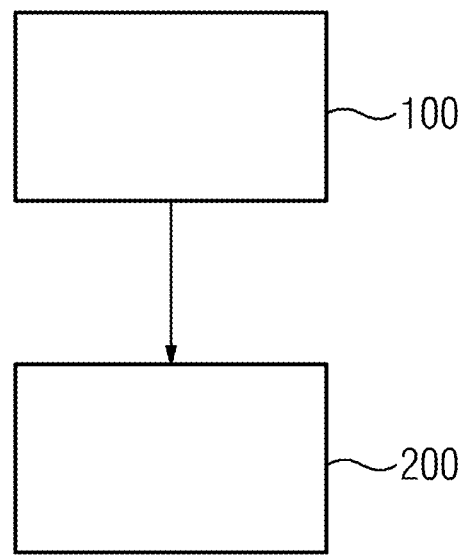
FIG. 6 is a flowchart of an embodiment of the method according to the invention.

FIG. 6 is a flowchart of a method according to the invention for a design of a first primary coil winding 41 and a second primary coil winding 42 of a first primary coil 40 of a gradient coil assembly 19. The gradient coil assembly 19 comprises the first primary coil 40 and a first secondary coil 50, wherein the first primary coil winding 41 and the second primary coil winding 42 are electrically connected to a first voltage source 71. The method according to the invention starts with method step 100, according to which a magnetic field gradient in a first direction is specified. Then, in method step 200, a geometry and/or an electric property of the first primary coil winding 41 and the second primary coil winding 42 is determined such that, on the induction of a first current through the first voltage source 71, the magnetic field gradient is generated in the first direction jointly by the first primary coil winding 41 and the second primary coil winding 42.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:
1. A gradient coil assembly comprising:
a first primary coil comprising a first primary coil winding and a second primary coil winding, the first primary coil winding being disposed from a center of the gradient coil assembly by a first radial distance, and the second primary coil winding being disposed from the center of the gradient coil assembly by a second radial distance that is different than the first radial distance;
a second primary coil comprising a third primary coil winding; and
a first secondary coil;
wherein said first primary coil winding and said second primary coil winding (i) have connections configured to electrically connect to a first voltage source, (ii) are jointly designed to generate a magnetic field gradient in a first direction when a first current is induced in said first primary coil winding and second primary coil winding by said first voltage source,
wherein the third primary coil winding (i) has a connection configured to electrically connect the third primary coil winding in series to a second voltage source, and (ii) is configured to generate a magnetic field gradient in a second direction when induced with a second current by said second voltage source,
wherein the third primary coil winding is disposed from a center of the gradient coil assembly by a third radial distance that is between the first radial distance and the second radial distance such that the third primary coil winding is disposed between the first primary coil winding and the second primary coil winding, and wherein the first secondary coil comprises only a first secondary coil winding, the first secondary coil winding having a connector configured to connect the first secondary coil winding in series to the first voltage source so as to screen the magnetic field gradient in the first direction when the first voltage source induces the first current in the first and second primary coil windings of the first primary coil.

2. A gradient coil assembly as claimed in claim 1, wherein:
when said first primary coil winding and second primary coil winding have said first current induced therein, a current density in at least one of said first primary coil winding and second primary coil winding is at most 70% of a current density in said third primary coil winding when said second current is induced in said third primary coil winding.

3. A gradient coil assembly as claimed in claim 1, comprising:
a first cooling layer assigned to said first primary coil winding and a second cooling layer assigned to said second primary coil winding.

4. A gradient coil assembly as claimed in claim 3, further comprising:
a third cooling layer assigned to said third primary coil winding.

5. A gradient coil assembly as claimed in claim 1, wherein said first primary coil winding and said second primary coil winding are connected in parallel to said first voltage source.

6. A gradient coil assembly as claimed in claim 1, wherein said first primary coil winding and said second primary coil winding are connected in series to said first voltage source.

7. A gradient coil assembly of claim 1, wherein the first primary coil winding and the second primary coil winding are separate coil windings that constitute a separation of the first primary coil.

8. A gradient coil assembly of claim 7, wherein the current induced in the first primary coil winding and second primary coil winding by the first voltage source is divided between the first primary coil winding and the second primary coil winding.

9. A gradient system comprising:
a gradient coil assembly comprising a first primary coil and a first secondary coil, said first primary coil comprising a first primary coil winding and a second primary coil winding, the first primary coil winding being disposed from a center of the gradient coil assembly by a first radial distance, and the second primary coil winding being disposed from the center of the gradient coil assembly by a second radial distance that is different than the first radial distance;
a second primary coil comprising a third primary coil winding;
a first voltage source electrically connected to said first primary coil winding and said second primary coil winding,
wherein said first primary coil winding and second primary coil winding are jointly designed to generate a magnetic field gradient in a first direction when induced with a first current by said first voltage source,
wherein the third primary coil winding (i) has a connection configured to electrically connect the third primary coil winding in series to a second voltage source, (ii) is configured to generate a magnetic field gradient in a second direction when induced with a second current by said second voltage source,
wherein the third primary coil winding is disposed from a center of the gradient coil assembly by a third radial distance that is between the first radial distance and the second radial distance such that the third primary coil winding is disposed between the first primary coil winding and the second primary coil winding, and
wherein the first secondary coil comprises only a first secondary coil winding, the first secondary coil winding having a connector configured to connect the first secondary coil winding in series to the first voltage source so as to screen the magnetic field gradient in the first direction when the first voltage source induces the first current in the first and second primary coil windings of the first primary coil.

10. A gradient system as claimed in claim 9, comprising:
a first cooling layer assigned to said first primary coil winding and a second cooling layer assigned to said second primary coil winding.

11. A magnetic resonance (MR) apparatus, comprising:
an MR data acquisition scanner; and
a gradient coil assembly, comprising:
a first primary coil and a first secondary coil, said first primary coil comprising a first primary coil winding and a second primary coil winding, the first primary coil winding being disposed from a center of the gradient coil assembly by a first radial distance, and the second primary coil winding being disposed from the center of the gradient coil assembly by a second radial distance that is different than the first radial distance;
a second primary coil comprising a third primary coil winding;
a first voltage source electrically connected to said first primary coil winding and said second primary coil winding,
wherein said first primary coil winding and second primary coil winding are jointly designed to generate a magnetic field gradient in a first direction when induced with a first current by said first voltage source,
wherein the third primary coil winding (i) has a connection configured to electrically connect the third primary coil winding in series to a second voltage source, (ii) is configured to generate a magnetic field gradient in a second direction when induced with a second current by said second voltage source, and
wherein the third primary coil winding is disposed from a center of the gradient coil assembly by a third radial distance that is between the first radial distance and the second radial distance such that the third primary coil winding is disposed between the first primary coil winding and the second primary coil winding, and
wherein the first secondary coil comprises only a first secondary coil winding, the first secondary coil winding having a connector configured to connect the first secondary coil winding in series to the first voltage source so as to screen the magnetic field gradient in the first direction when the first voltage source induces the first current in the first and second primary coil windings of the first primary coil.

12. An MR apparatus as claimed in claim 11, wherein said MR data acquisition scanner comprises a basic field magnet and a radio-frequency antenna, and
wherein said first primary coil winding and said second primary coil winding are contained within a hollow cylindrical spacing between said basic field magnet and said radio-frequency antenna.

13. A magnetic resonance (MR) apparatus as claimed in claim 11, comprising:
a first cooling layer assigned to said first primary coil winding and a second cooling layer assigned to said second primary coil winding.

14. A method for designing a first primary coil winding and a second primary coil winding of a first primary coil of a gradient coil assembly that comprises a first secondary coil and a second primary coil comprising a third primary coil winding,
wherein said first primary coil winding and said second primary coil winding are configured to electrically connect to a first voltage source, the first primary coil winding being disposed from a center of the gradient coil assembly by a first radial distance, and the second primary coil winding being disposed from the center of the gradient coil assembly by a second radial distance that is different than the first radial distance, and
wherein said third primary coil winding is configured to electrically connect the third primary coil winding in series to a second voltage source, the third primary coil winding being disposed from a center of the gradient coil assembly by a third radial distance that is between the first radial distance and the second radial distance such that the third primary coil winding is disposed between the first primary coil winding and the second primary coil winding, and said method comprising:
providing a computer with an electronic specification of a magnetic field gradient in a gradient direction;
in said computer, determining one of a geometric property or an electrical property of said first primary coil winding, said second primary coil winding, and said third primary coil winding so as to cause, (i) when a first current is induced in said first primary coil winding and said second primary coil winding by said first voltage source, said magnetic field gradient to be generated in said gradient direction jointly by said first primary coil winding and said second primary coil winding, and (ii) when a second current is induced in said third primary coil winding by said second voltage source, a magnetic field gradient to be generated in a second direction; and
manufacturing said gradient coil assembly with said first primary coil winding, said second primary coil winding, and said third primary coil winding having the determined at least one of the geometric or the electrical property,
wherein the first secondary coil comprises only a first secondary coil winding, the first secondary coil winding having a connector configured to connect the first secondary coil winding in series to the first voltage source so as to screen the magnetic field gradient in the gradient direction when the first voltage source induces the first current in the first and second primary coil windings of the first primary coil.

* * * * *